US008221346B2

(12) United States Patent
Sakata et al.

(10) Patent No.: US 8,221,346 B2
(45) Date of Patent: Jul. 17, 2012

(54) BLOOD SUGAR LEVEL CONTROL SYSTEM

(75) Inventors: Tetsuya Sakata, Kyoto (JP); Yoshiharu Uehata, Kyoto (JP); Hitoshi Hata, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 12/937,520

(22) PCT Filed: Apr. 24, 2009

(86) PCT No.: PCT/JP2009/058133
§ 371 (c)(1),
(2), (4) Date: Oct. 12, 2010

(87) PCT Pub. No.: WO2009/131205
PCT Pub. Date: Oct. 29, 2009

(65) Prior Publication Data
US 2011/0046548 A1    Feb. 24, 2011

(30) Foreign Application Priority Data
Apr. 24, 2008  (JP) .................................. 2008-114548

(51) Int. Cl.
*A61M 5/00*   (2006.01)
(52) U.S. Cl. ......................................................... 604/67
(58) Field of Classification Search .................. 604/65, 604/66, 67, 131, 151; 600/316, 347, 365
See application file for complete search history.

(56) References Cited

U.S. PATENT DOCUMENTS
5,665,065 A    9/1997    Colman et al.
5,995,860 A    11/1999   Sun et al.
6,049,727 A    4/2000    Crothall
6,379,317 B1   4/2002    Kintzig et al.
6,999,685 B1   2/2006    Kawase et al.
(Continued)

FOREIGN PATENT DOCUMENTS
JP     2004-024699    1/2004
(Continued)

OTHER PUBLICATIONS
International Search Report dated May 26, 2009 issued to international application No. PCT/JP2009/058133.
(Continued)

*Primary Examiner* — Nicholas Lucchesi
*Assistant Examiner* — Aarti B Berdichevsky
(74) *Attorney, Agent, or Firm* — Knobbe Martens Olson & Bear LLP

(57) ABSTRACT

The present invention relates to a blood sugar level control system equipped with an insulin dispensing device 2 and a blood sugar measuring device 3. An attachment mechanism 4 is provided which serves to couple the insulin dispensing device 2 and said blood sugar measuring device 3 in a relatively movable manner. Preferably, the attachment mechanism 4 is constructed so that the blood sugar measuring device 3 is movable or slidable with respect to the insulin dispensing device 2. A blood sugar level control system can be provided which includes a blood sugar measuring device and an insulin dispensing device without using an adapter. Accordingly, it is possible to avoid a cost rise due to an increase in the number of parts as required. In addition, it is possible to prevent the blood sugar level control system from being unable to be used due to the loss of an adapter in the form of a different part.

10 Claims, 16 Drawing Sheets

U.S. PATENT DOCUMENTS

| | | | |
|---|---|---|---|
| 7,519,408 B2 * | 4/2009 | Rasdal et al. | 600/347 |
| 7,591,801 B2 * | 9/2009 | Brauker et al. | 604/161 |
| 7,722,536 B2 * | 5/2010 | Goodnow | 600/365 |
| 7,753,879 B2 * | 7/2010 | Mernoe | 604/131 |
| 7,976,492 B2 * | 7/2011 | Brauker et al. | 604/65 |
| 8,029,443 B2 * | 10/2011 | Goodnow | 600/365 |
| 8,029,459 B2 * | 10/2011 | Rush et al. | 604/65 |
| 8,029,460 B2 * | 10/2011 | Rush et al. | 604/65 |
| 2003/0088238 A1 | 5/2003 | Poulsen et al. | |
| 2003/0122021 A1 | 7/2003 | McConnell et al. | |
| 2004/0254434 A1 | 12/2004 | Goodnow et al. | |
| 2005/0126938 A1 | 6/2005 | Uehata | |
| 2005/0192557 A1 | 9/2005 | Brauker et al. | |
| 2008/0060955 A1 * | 3/2008 | Goodnow | 206/305 |
| 2009/0048501 A1 * | 2/2009 | Goodnow | 600/316 |
| 2009/0082654 A1 | 3/2009 | Goodnow et al. | |
| 2010/0256565 A1 * | 10/2010 | Mernoe et al. | 604/152 |

FOREIGN PATENT DOCUMENTS

| | | |
|---|---|---|
| JP | 2005-514095 | 5/2005 |
| JP | 2005-296428 | 10/2005 |
| JP | 2006-061739 | 3/2006 |
| JP | 2007-503288 | 2/2007 |
| JP | 2007-525276 | 9/2007 |
| WO | WO 91/18548 | 12/1991 |
| WO | WO 03/068071 | 8/2003 |

OTHER PUBLICATIONS

Accu-Check Smart Pix system downloaded from website on Dec. 28, 2007 http://www.accu-check.jp/medical/products/data_management/smart_pix/smart_pix.htm in 5 pages with partial translation.

* cited by examiner

FIG.5A
FIG.5B
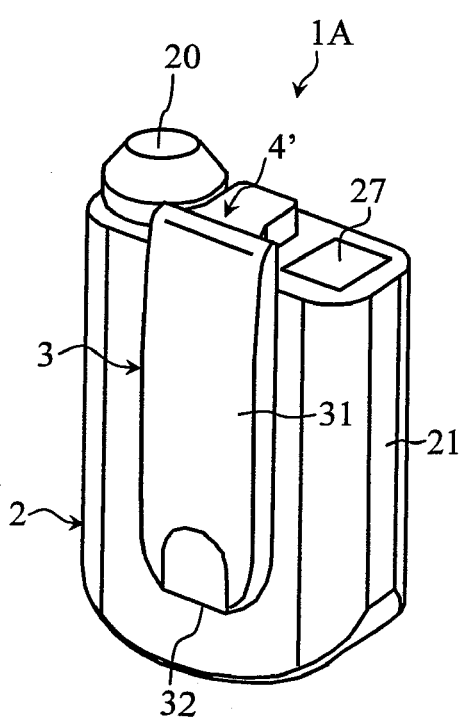
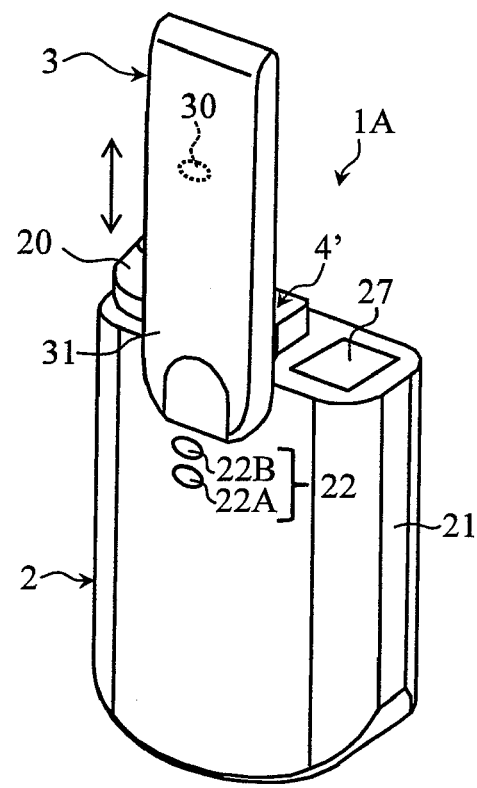

BLOOD SUGAR LEVEL CONTROL SYSTEM

TECHNICAL FIELD

The present invention relates to a blood sugar level control system including a blood sugar measuring device and an insulin dispensing device.

BACKGROUND ART

It is important to maintain a blood sugar level within a normal range for the purpose of preventing complications of diabetes such as diabetic retinopathy, diabetic nephropathy, diabetic neuropathy, and the like. Some diabetic patients require insulin administration in order to maintain their blood sugar levels within a desirable range. These diabetic patients usually administer insulin to themselves by the use of a syringe while monitoring their blood sugar levels. By means of the insulin administration with a syringe, the concentration of insulin in a bloodstream increases at the time of the administration of insulin. However, by means of the administration of insulin with the syringe, it is difficult to cause insulin of low concentration to exist in the bloodstream over a long period of time, just as the behavior or action of a pancreas in a living body.

In recent years, there has been used an insulin dispensing device which controls the injection volume of insulin in an automatic manner. The insulin dispensing device is one in which the dispensing volume and timing of insulin are programmed. By means of this insulin dispensing device, it is possible to inject insulin in a slow or gradual manner over a long period of time under nearer physiological conditions, and for this reason, such an insulin dispensing device is effective for maintaining the blood sugar level in a desired range. Insulin dispensing devices have been made smaller in size and lighter in weight, and it has also been carried out that a diabetic patient wears such a miniaturized insulin dispensing device on his or her body.

On the other hand, in general, monitoring of the blood sugar level is performed by measuring the blood sugar level in a periodic manner with the use of a small-sized blood sugar measuring device adopting an in vitro measuring method.

A typical small-sized blood sugar measuring device uses a specimen holding a glucose oxidation-reduction enzyme. The measurement of a blood sugar level by the use of a small-sized blood sugar measuring device is carried out by inserting a specimen into an insertion opening of the small-sized blood sugar measuring device, and by supplying a blood sample, which was obtained by lancing the skin of a fingertip or the like with the use of a portable lancing device, onto the specimen. As a result of this, in the small-sized blood sugar measuring device, the blood sugar level can be calculated based on an amount of charge transfer or a coloration level resulting from enzyme reactions inside the specimen.

At present, there are cases where, by using a small-sized blood sugar measuring device and an insulin dispensing device together, the dispensing volume of insulin into blood is adjusted in accordance with the monitored result of the blood sugar level by the small-sized blood sugar measuring device (see, for example, a Patent Document 1 and a Patent Document 2).

An insulin dispensing device equipped with a blood sugar measuring function is disclosed in the Patent Document 1. Such an insulin dispensing device becomes large in size, so in cases where the insulin dispensing device is used while being worn on the body of a user, the burden of the user is heavy. In addition, under the environment in which the insulin dispensing device becomes in contact with water, such as at the time of bathing, etc., it is not only necessary to make the device water-proof, but also there exists a large possibility that water will enter the interior of the device because of the presence of the insertion opening for inserting a specimen.

An apparatus including an insulin dispensing device and a small-sized blood sugar measuring device and an adapter for combining them is disclosed in the Patent Document 2. In this apparatus, by combining the small-sized blood sugar measuring device with the insulin dispensing device, the result of the measurement of the blood sugar level made by the small-sized blood sugar measuring device is transmitted to the insulin dispensing device. General-purpose short-distance wireless communication means such as an infrared ray communication means is adopted for data transmission of the measurement result. In such an apparatus, in a situation, such as at the time of bathing, etc., where the insulin dispensing device is in contact with water, or in a situation where the small-sized blood sugar measuring device is not used, the small-sized blood sugar measuring device can be separated from the insulin dispensing device, so the user's burden is reduced. On the other hand, because the adapter is required for the data transmission, there is a high risk of being unable to carry out data transmission from the small-sized blood sugar measuring device to the insulin dispensing device due to a loss of the adapter. In addition, the use of the adapter increases the number of parts as required, and hence becomes a cause of increasing the cost of manufacture or complicating the attaching and detaching operation of the small-sized blood sugar measuring device with respect to the insulin dispensing device.

In cases where the blood sugar level is controlled by the use of the small-sized blood sugar measuring device and the insulin dispensing device, measurement data and data corresponding to the history with respect to the dispensing or delivery of insulin are outputted from these devices to an external information processing device. General-purpose short-distance wireless communication means such as an infrared ray communication means is adopted in many cases for communication to such an information processing device, too.

However, in the case of adopting short-distance wireless communication means, it is necessary to arrange the communication ports of the insulin dispensing device and the small-sized blood sugar measuring device faces (opposes) each other. Therefore, with the configuration in which the small-sized blood sugar measuring device is combined with the insulin dispensing device, at the time when data is transmitted from the insulin dispensing device to the external information processing device, the small-sized blood sugar measuring device may become an obstacle depending on the position of the communication port in the insulin dispensing device, so the data may not be able to be transmitted. In particular, in the insulin dispensing device, in the case of making use of its communication port, which is usually used for communication with the small-sized blood sugar measuring device, for the purpose of data transmission to the external information processing device, the small-sized blood sugar measuring device becomes an obstacle for communication. In order to eliminate such inconveniences, it is only necessary to separate the small-sized blood sugar measuring device from the insulin dispensing device, but in that case, not only the operation of separating the small-sized blood sugar measuring device is troublesome, but also the possibility of losing the adapter and the blood sugar measuring device becomes high.
Patent Document 1: Japanese translation of PCT international application No. 11-507250

Patent Document 2: Japanese translation of PCT international application No. 2007-503288

DISCLOSURE OF THE INVENTION

Problem to be Solved by the Invention

An object of the present invention is to provide a blood sugar level control system which can be made to perform data transmission from a blood sugar measuring device to an insulin dispensing device by a simple operation.

Another object of the present invention is to provide a blood sugar level control system which is capable of preventing the missing or loss of a blood sugar measuring device and the like.

Means for Solving the Problems

The present invention relates to a blood sugar level control system that is provided with a blood sugar measuring device for measuring a blood sugar level, and an insulin dispensing device for administering insulin to the inside of a body.

The blood sugar level control system is further provided with an attachment mechanism which serves to couple said insulin dispensing device and said blood sugar measuring device with each other in a relatively movable manner, and which is provided on said insulin dispensing device and said blood sugar measuring device.

Preferably, the attachment mechanism couples the blood sugar measuring device to said insulin dispensing device in a rotatable or slidable manner without separating the insulin dispensing device and said blood sugar measuring device from each other.

The blood sugar level measuring system may be further provided with a wireless data communication unit. The wireless data communication unit includes, for example, a first wireless data communication part that is installed in said blood sugar measuring device so as to transmit data from said blood sugar measuring device to the insulin dispensing device, and a second wireless data communication part that is installed in the insulin dispensing device so as to receive data from the first wireless data communication part and to perform data communication with an external information processing device.

The attachment mechanism is constructed in such a manner that when data communication between the second wireless data communication part and the information processing unit is carried out, for example, it can move the blood sugar measuring device to a position in which the blood sugar measuring device does not block data communication by the second wireless data communication part.

The blood sugar level control system may further have a second blood sugar measuring device that is used while being implanted in the inside of the body. In this case, at least one of the blood sugar measuring device and the insulin dispensing device is constructed so as to be able to perform data communication with the second blood sugar measuring device.

The second wireless data communication part is made possible to perform data communication with the second blood sugar measuring device, for example. It is preferable that the insulin dispensing device be further provided with a selection unit for selecting the blood sugar measuring device or the second blood sugar measuring device as a communication object. The selection unit is constructed so as to be able to select the information processing unit as the communication object, for example.

The selection unit is, for example, a switch that is arranged in the insulin dispensing device. The selection unit may select the communication object according to the relative position of the blood sugar measuring device to the insulin dispensing device. The selection unit in this case includes a plurality of switches, for example, and it is constructed so as to select the communication object according to combinations of an on state or an off state of each of the plurality of switches.

It is preferable that the blood sugar measuring device and the insulin dispensing device be each provided with a housing having a waterproof property or a water resistant property.

It is preferable that the blood sugar measuring device be provided, for example, with an insertion opening for inserting a specimen, and a closing unit for closing the insertion opening.

Advantageous Effect of the Invention

According to the present invention, the attachment mechanism is provided between the blood sugar measuring device and the insulin dispensing device, so the blood sugar level control system can be provided which includes the blood sugar measuring device and the insulin dispensing device, but does not include an adapter that is a part that can be separated from other parts. Therefore, it is possible to avoid a cost rise due to an increase in the number of parts as required. In addition, it is also possible to reduce the possibility of losing the adapter (a separable part) or the blood sugar measuring device.

Further, in the present invention, if the blood sugar measuring device and the insulin dispensing device are made movable relative to each other without being mutually separated from each other, it will be possible to prevent the loss of the blood sugar measuring device, and at the same time the attachment and detachment of the blood sugar measuring device with respect to the insulin dispensing device will not be required. As a result, the burden of the user is reduced.

BRIEF DESCRIPTION OF THE DRAWINGS

FIG. 5A and FIG. 5B are perspective views showing other examples of an attachment mechanism in the blood sugar level control system shown in FIG. 1.

Figure 1A:
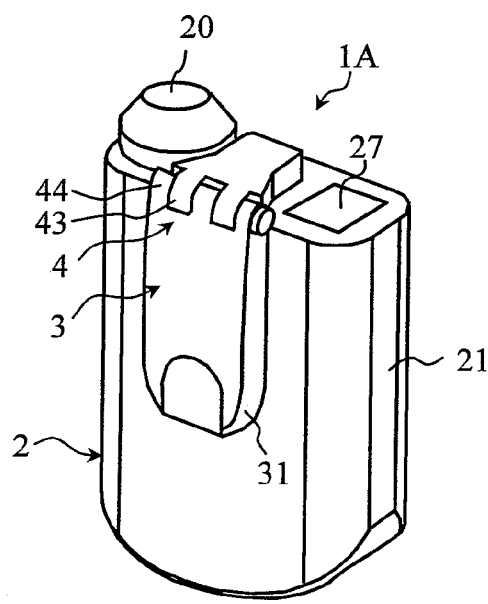
FIG. 1A and FIG. 1B are perspective views showing a blood sugar level control system according to a first embodiment of the present invention.

DESCRIPTION OF THE REFERENCE SIGNS 1A, 1B, 1C: Blood sugar level control systems
2: Insulin dispensing device
3: Blood sugar measuring device
4, 4', 4": Attachment mechanisms
5A: Specimen
5B: Cap
6: Information processing device
7: Continuous blood sugar measuring device (second blood sugar measuring device)
22: Communication part (of the insulin dispensing device)
28: Switch
28A: First switch
28B: Second switch
30: Communication part (of the blood sugar measuring device)
21: Housing (of the insulin dispensing device)
31: Housing (of the blood sugar measuring device)
32: Specimen insertion opening

THE BEST MODE FOR CARRYING OUT THE INVENTION

Hereinafter, embodiments according to the present invention will be described with reference to the accompanying drawings.

First, a first embodiment of a blood sugar level control system of the present invention will be described, while referring to FIG. 1 through FIG. 4.

Figure 1B:
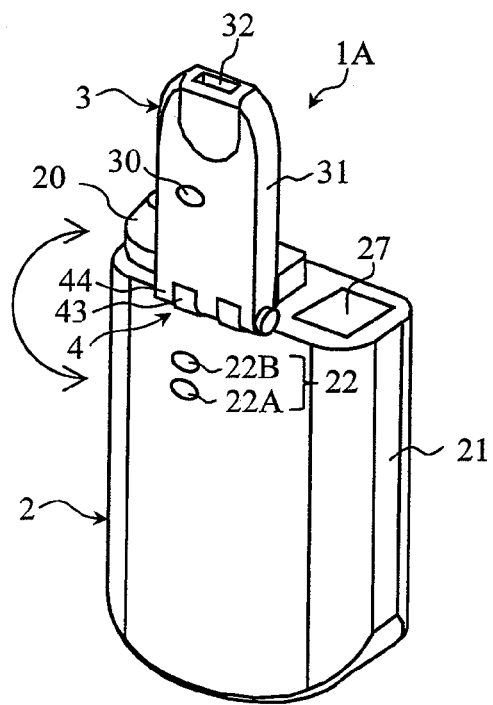

As shown in FIG. 1A and FIG. 1B, a blood sugar level control system 1A includes an insulin dispensing device 2 and a blood sugar measuring device 3, wherein the insulin dispensing device 2 and the blood sugar measuring device 3 are configured so that data communication between them can be performed. This blood sugar level control system 1A is a system that determines, based on measurement data from the blood sugar measuring device 3, whether it is necessary to perform the administration of insulin to the inside of a living body, and, if necessary, calculate an amount of insulin to be administered based on the measurement data, and administers the calculated amount of insulin.

The insulin dispensing device 2 is to administer insulin to the inside of the body, and it is fixedly attached to a skin of an abdominal part or a shoulder, for example. The insulin dispensing device 2 may instead be fixedly attached to clothing or may be carried in other ways. This insulin dispensing device 2 is provided with an insulin delivery part 20, a housing 21, and a communication part 22.

The insulin delivery part 20 is a part which discharges or delivers the insulin retained in the inside of the device to the outside thereof, and is, for example, a part to which a needle tube (not shown) is connected. The needle tube has a needle portion that is usually adapted to be inserted into a portal artery connected with a liver, or into a peritoneal space which is close to the liver. As a result of this, the insulin from the insulin delivery part 20 is delivered or sent out to the portal arterial system through the tube, and the insulin is carried to the liver through the portal arterial system.

The housing 21 forms the contour of the insulin dispensing device 2, and accommodates therein a circuit board which can perform calculations for controlling the operations of the respective component parts. It is preferable that this housing 21 have a waterproof property or a water resistant property. The housing 21 is made to have waterproofness or water resistance by the use of a material with extremely low permeability, such as for example a polypropylene (PP) resin, and by providing a wall thickness of 1 mm or more.

The communication part 22 includes a transmitting part 22A and a receiving part 22B. The transmitting part 22A is to send data to an information processing device 6 (see FIG. 2), and the receiving part 22B is to receive data from the blood sugar measuring device 3 and the information processing device 6 (see FIG. 2). As the communication part 22, there can be used one which consists of a package, and a light oscillation element and a light receiving element integrated into the package, for example. Although the transmission and reception of data in the communication part 22 can be performed, for example, by the use of infrared light, light of other frequencies (wavelengths), a radio wave such as a 2.45 GHz band adopted in Bluetooth may be used.

Figure 2:
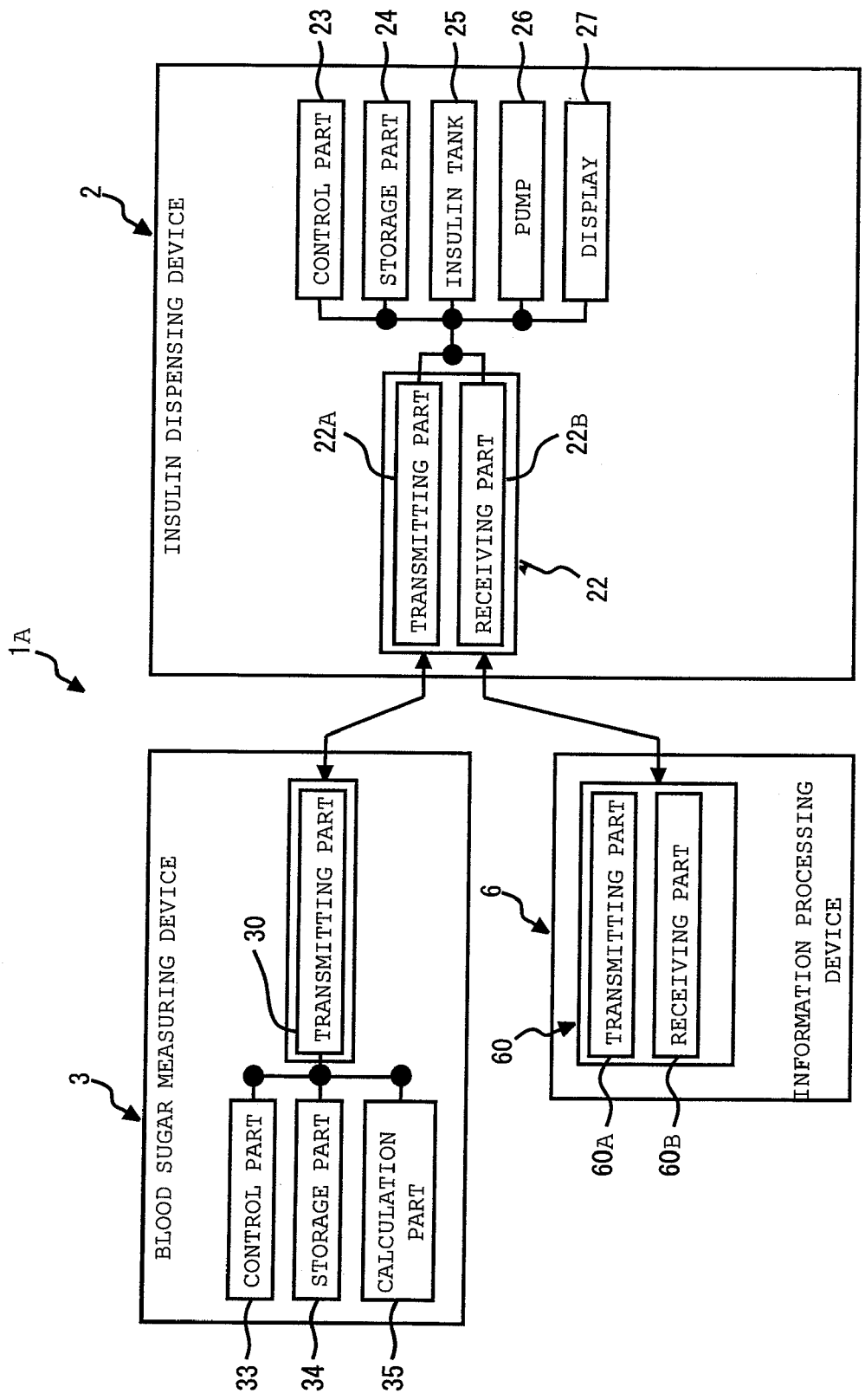
FIG. 2 is a block diagram showing the blood sugar level control system shown in FIG. 1, together with an information processing unit.

As shown in FIG. 2, the insulin dispensing device 2 further has a control part 23, a storage part 24, an insulin tank 25, a pump 26, and a display 27.

The control part 23 controls the operations of the respective parts (e.g., on/off operation of the pump 26, data transmission from the transmitting part 22A, or an operation of storing the reception data received in the receiving part 22B in the storage part 24).

The storage part 24 stores data required for the drive of the pump 26. This storage part 24 further stores, for example, measurement data transmitted from the blood sugar measuring device 3, and data with respect to the delivery history of insulin which has been made to correspond to the blood sugar level. That is, the blood sugar level data and the data with respect to the delivery history of insulin stored in the storage part 24 from the insulin dispensing device 2 to the information processing device 6 are transmitted.

The insulin tank 25 is to hold insulin, and is connected to the insulin delivery part 20 through the tube (illustration thereof omitted).

The pump 26 is to provide a driving force for conveying the insulin in the insulin tank 25. As the pump 26, a variety of kinds of well-known ones such as, for example, a syringe pump, can be used.

The display 27 is to display a variety of kinds of information (e.g., the delivery state of insulin, the remaining amount of insulin, or the measurement data transmitted from the blood sugar measuring device 3).

As shown in FIG. 1A and FIG. 1B, the blood sugar measuring device 3 is to measure the concentration of glucose in blood, and is coupled to the insulin dispensing device 2 through an attachment mechanism 4 for rotation relative thereto. This blood sugar measuring device 3 is provided with a communication part 30 and a housing 31.

The communication part 30 functions as a transmitting part for transmitting the measurement data to the insulin dispensing device 2, and is incorporated in the interior of the housing 31. The communication part 30 may have a mechanism for receiving data. This communication part 30 is able to perform data transmission through the use of infrared light. Of course, for the purpose of transmission of data from the communication part 30, light of other frequencies (wavelengths), or a radio wave such as a 2.45 GHz band adopted in Bluetooth, may be used.

Here, the "measurement data" transmitted from the communication part 30 includes raw data such as a current value measured in the blood sugar measuring device 1, data obtained by converting the raw data into other physical quantities such as a voltage value, data with respect to the calculated result of the blood sugar level, and data obtained by correcting the raw data and blood sugar level calculation data. The communication part 30 may transmit, in addition to the measurement data, data for correcting the raw data and the blood sugar level data, such as for example the manufactured lot number of a specimen, a measured temperature, and a separately measured hematocrit value, as well as correction information required for the determination of the blood sugar level.

The housing 31 forms the contour of the blood sugar measuring device 3. The housing 31 accommodates a circuit board capable of performing calculations for controlling the operations of the respective parts, and at the same time has a specimen insertion opening 32.

It is preferable that the housing 31 have a waterproof property or a water resistant property. Such a housing 31 can be formed by using a material with extremely low permeability, such as for example a polypropylene (PP) resin, and by providing a wall thickness of 1 mm or more, similar to the housing 21 of the insulin dispensing device 2.

Figure 3A:
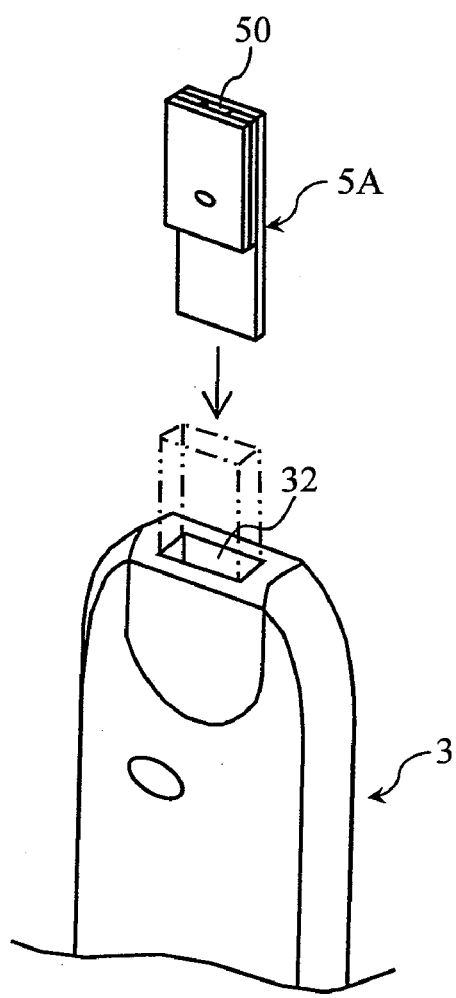
FIG. 3A is a perspective view showing a state in which a specimen has been inserted into a blood sugar measuring device shown in FIG. 1.

As shown in FIG. 3A, the specimen insertion opening 32 is a part through which a specimen 5A is inserted. The specimen 5A is to measure the blood sugar level, and is a glucose sensor with a capillary 50 in which an oxidation-reduction enzyme is accommodated. The capillary 50 is a part which serves to draw and hold blood. This specimen 5A can indicate the amount of electron transfer at the time when glucose is oxidized or reduced by the catalytic action of the oxidation-reduction enzyme as a response current or coloration of the reagent.

Figure 3B:
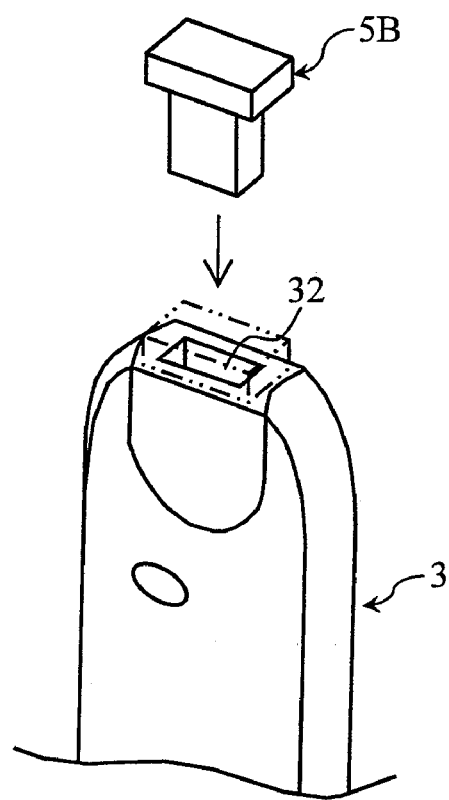
FIG. 3B is a perspective view showing a state in which a cap has been inserted.

When the blood sugar measuring device 3 is not used, a cap 5B may be inserted into the specimen insertion opening 32, as shown in FIG. 3B. The cap 5B is formed of a material having waterproofness in such a manner that it can close the specimen insertion opening 32. Therefore, when the blood sugar measuring device 3 is not used, the invasion of water into the blood sugar measuring device 3 can be prevented by the use of the cap 5B. Accordingly, even under an environment in which the blood sugar measuring device 3 is in contact with water such as at the time of taking a bath, etc., it is possible to prevent water from invading into the blood sugar measuring device 3, without removing the blood sugar measuring device 3 from the insulin dispensing device 2, as a result of which convenience is improved.

Any member/configuration for closing the specimen insertion opening 32 can be adopted in place of the cap 5B. For example, there can be adopted a configuration provided with a lid which serves to close the specimen insertion opening 32 when the specimen 5A is not inserted, and which is pushed in when the specimen 5A is being inserted or has been inserted. As a result of this, the invasion of water into the blood sugar measuring device 3 can be suppressed even if the cap 5B is not used.

As shown in FIG. 2, the blood sugar measuring device 3 further has a control part 33, a storage part 34, and a calculation part 35.

The control part 33 controls the operations of the respective parts (e.g., data transmission from the communication part (transmitting part) 30 or the calculation operation of the blood sugar level in the calculation part 35).

The storage part 34 stores data required for the measurement of the blood sugar level (e.g., measurement data such as a current value, etc., data with respect to a calibration curve, and correction data). This storage part 34 can store the measurement result of the blood sugar level.

The calculation part 35 calculates the blood sugar level based on the data obtained from the specimen 5A. The calculation of the blood sugar level is performed based on raw data (or conversion data which is obtained through the conversion of the raw data), correction data, and calibration curve data. However, the calculation of the blood sugar level from the measured data may also be carried out in the insulin dispensing device 2.

Figure 4:
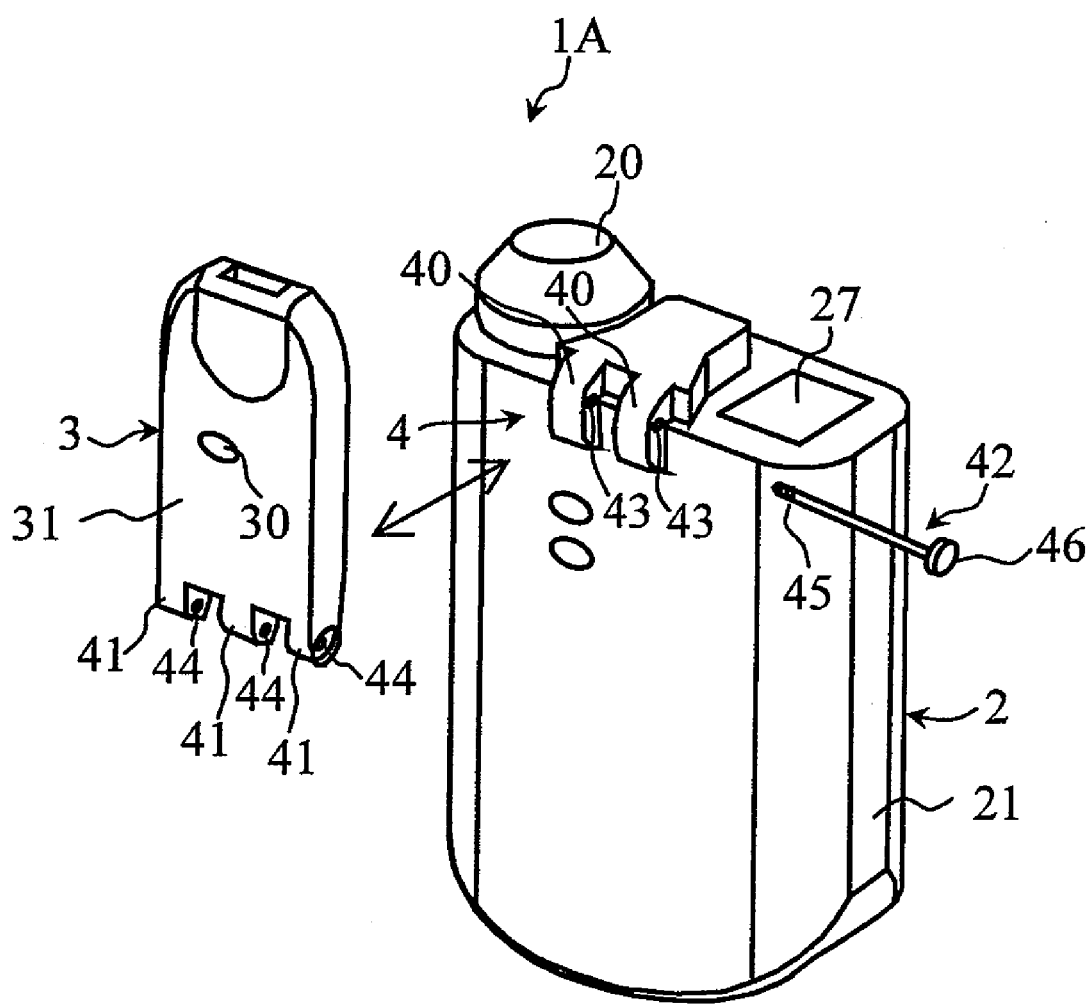
FIG. 4 is a perspective view showing a state in which the blood sugar measuring device has been separated from the insulin dispensing device in the blood sugar level control system shown in FIG. 1.

As shown in FIG. 1A, FIG. 1B and FIG. 4, the attachment mechanism 4 includes an attachment part 40 fixed to the insulin dispensing device 2, an attachment part 41 fixed to the blood sugar measuring device 3, and a pin 42. The attachment parts 40, 41 have the through holes 43, 44, respectively. These through holes 43, 44 are parts through which the pin 42 is inserted. The pin 42 has a threaded portion 45 which are provided in its tip end portion and a head portion 46. That is, the attachment mechanism 4 couples the blood sugar measuring device 3 to the insulin dispensing device 2 in a state in which the attachment parts 40, 41 are aligned with each other, by inserting the pin 42 into the through holes 43, 44, and manipulating the head portion 46 of the pin 42 to threadedly engage it with the threaded portion 45.

Thus, the blood control system 1A has a configuration capable of rotating the blood sugar measuring device 3 by means of the attachment mechanism 4, without separating the blood sugar measuring device 3 from the insulin dispensing device 2. As a result, it is possible to make selection between a state in which the communication part 30 of the blood sugar measuring device 3 faces the receiving part 22B of the insulin dispensing device 2, as shown in FIG. 1A, and a state in which the communication part 22 of the insulin dispensing device 2 can perform communications without being interfered or blocked by the blood sugar measuring device 3, as shown in FIG. 1B.

In the state shown in FIG. 1A, the transmitting part 22B of the blood sugar measuring device 3 faces the receiving part 22B of the insulin dispensing device 2, so measurement data can be transmitted from the transmitting part 30 of the blood sugar measuring device 3 to the receiving part 22B of the insulin dispensing device 2.

On the other hand, in the state shown in FIG. 1B, the communication part 22 of the insulin dispensing device 2 is exposed, so the insulin dispensing device 2 can perform data communication with the information processing device 6 (see FIG. 2) without being interfered or blocked by the blood sugar measuring device 3. That is, the calculation data of the blood sugar level or the delivery history of insulin, etc., can be transmitted from the transmitting part 22A of the insulin dispensing device 2 to the receiving part 60B of the information processing device 6. As a result of this, in the information processing device 6, the management of the blood sugar level can be carried out, and at the same time, a change in the amount of insulin to be administered, etc., can be considered. In addition, from the transmitting part 60A of the information processing device 6, a signal to perform data communication or data with respect to the change in the amount of insulin to be administered can be transmitted to the receiving part 22B of the insulin dispensing device 2.

As shown in FIG. 4, in the attachment mechanism 4, the blood sugar measuring device 3 can also be detached or removed from the insulin dispensing device 2 by rotating the head part 46 to release the threaded engagement of the threaded portion 45. Thus, by making it possible to detach the blood sugar measuring device 3 from the insulin dispensing device 2 in an easy and simple manner, the blood sugar measuring device 3 can be maintained in an easy and simple manner, and it is convenient in preventing the invasion of water from the specimen insertion opening 32 at the time of bathing.

Here, note that although the information processing device 6 is typically a personal computer, it includes a wristwatch type display device which a patient wears on his or her arm or wrist, and data control equipment or the like which is connected to a personal computer, etc., through a USB connection, etc.

Figure 10A:
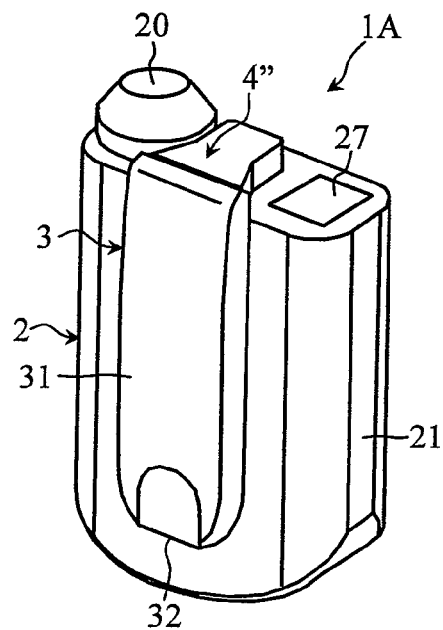
FIG. 10A and FIG. 10B are perspective views showing other examples of the attachment mechanism in the blood sugar level control system shown in FIG. 1.
Figure 10B:
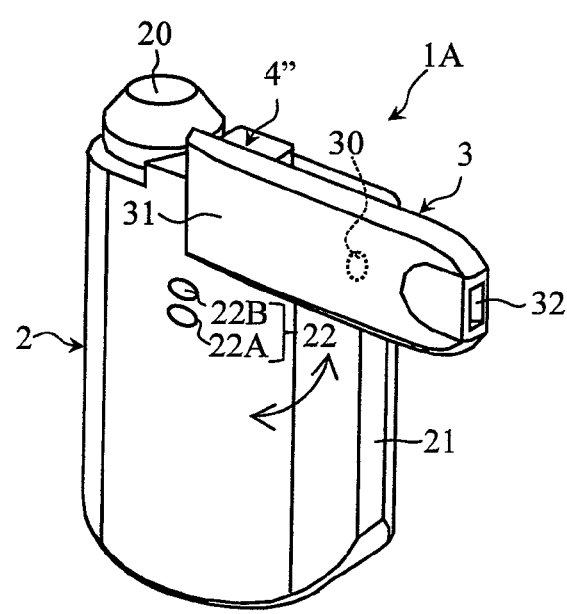
Figure 11:
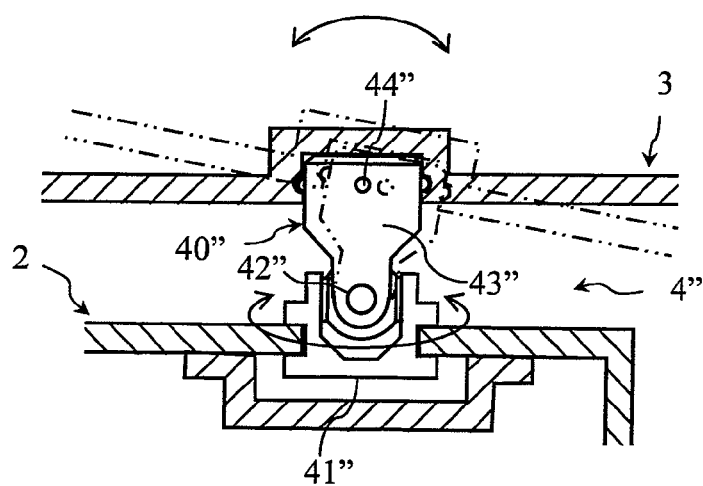
FIG. 11 is a perspective view explaining an operation of the attachment mechanism shown in FIG. 10.
Figure 12:
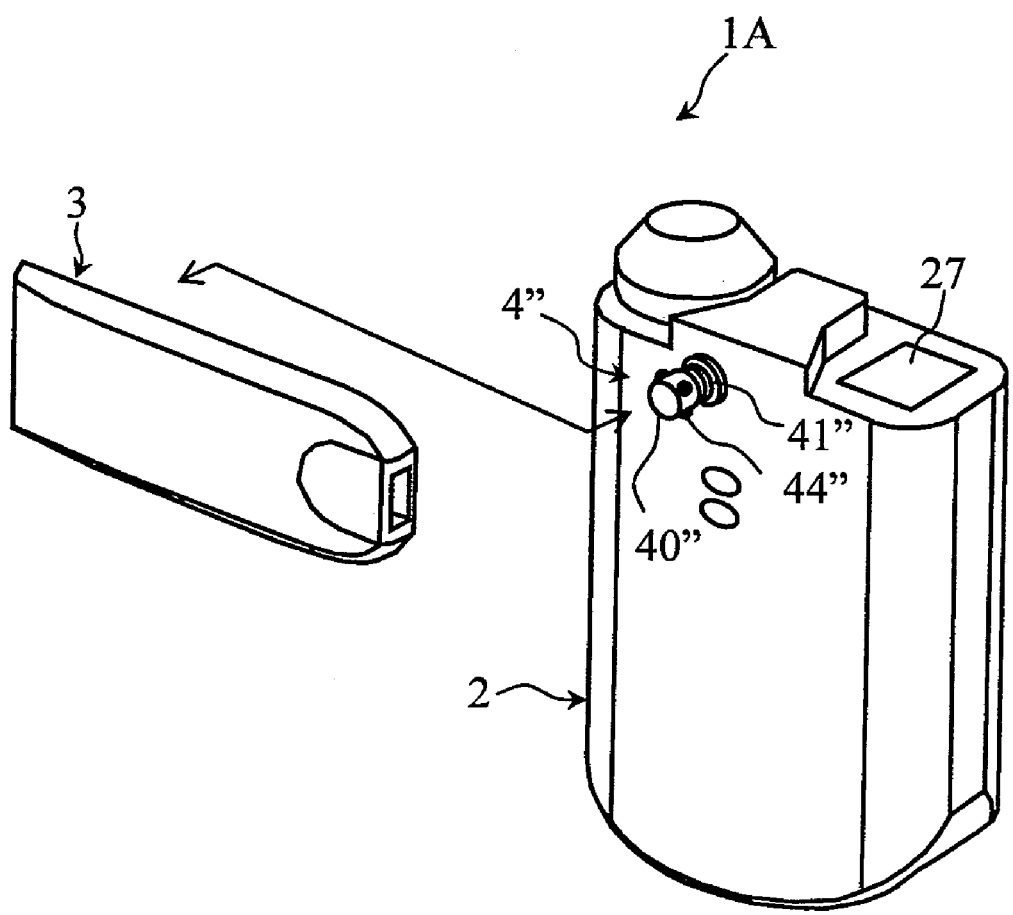
FIG. 12 is a perspective view showing a state in which the blood sugar measuring device has been separated from the insulin dispensing device in the blood sugar level control system shown in FIG. 10.

As the attachment mechanism 4, there can be adopted, in place of the construction shown in FIG. 1A and FIG. 1B, a construction denoted by a symbol 4' in FIG. 5 through FIG. 9, or a construction denoted by a symbol 4" in FIG. 10 through FIG. 12. However, in FIG. 5 through FIG. 12, the same symbols are attached to the same or similar elements to those in the blood sugar control system 1 and the information processing device 6 which have previously explained with reference to FIG. 1 through FIG. 4, and a duplication explanation thereof in the following will be omitted.

An attachment mechanism 4' shown in FIG. 5 through FIG. 9 serves to couple the insulin dispensing device 2 and the blood sugar measuring device 3 with each other in a relatively slidable manner without separating the blood sugar measuring device 3 with respect to the insulin dispensing device 2. In the blood sugar control system 1A which adopts this attachment mechanism 4', by causing the blood sugar measuring device 3 to slide relative to the insulin dispensing device 2, it is possible to make selection between a state in which the communication part 30 of the blood sugar measuring device 3 faces the receiving part 22B of the insulin dispensing device 2, as shown in FIG. 5A, and a state in which the communication part 22 of the insulin dispensing device 2 can perform communications without being interfered or blocked by the blood sugar measuring device 3, as shown in FIG. 5B. That is, in the blood sugar level measuring system 1A which adopts the attachment mechanism 4', too, it is possible to make selection between a state in which measurement data, etc., is transmitted from the blood sugar measuring device 3 to the insulin dispensing device 2, and a state in which data communication is carried out between the insulin dispensing device 2 and the information processing device 6.

Figure 6A:
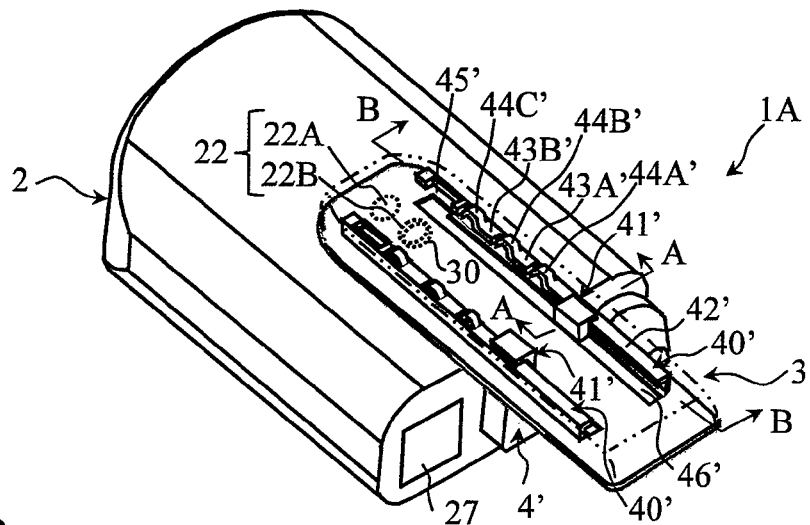
FIG. 6A through FIG. 6C are perspective views explaining an operation of the attachment mechanism shown in FIG. 5.
Figure 6B:
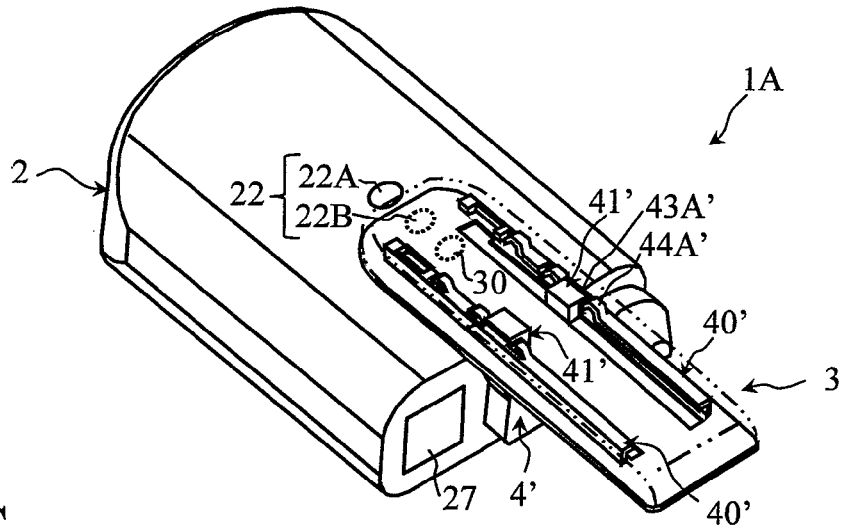
Figure 6C:
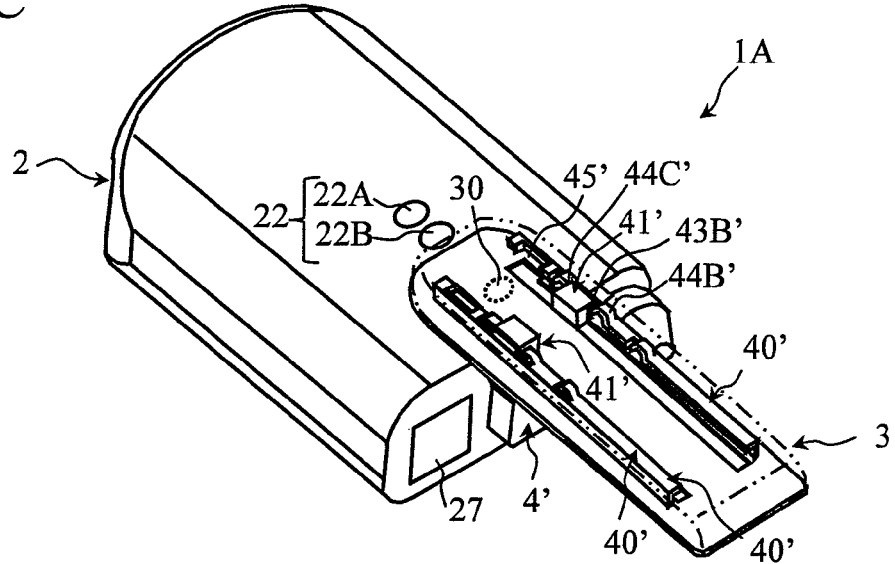

As shown in FIG. 6A through FIG. 6C, the attachment mechanism 4' is equipped with rails 40' which are formed on the blood sugar measuring device 3 and engagement parts 41' which are formed on the insulin dispensing device 2.

Each rail 40' has a smooth portion 42', concave portions 43A', 43B' and convex portions 44A', 44B', 44C'. The concave portions 43A', 43B' are located between adjacent ones of the convex portions 44A', 44B', 44C', respectively. The convex portions 44A', 44B', 44C' are processed so as to have a spring property. The spring property of the convex portions 44A', 44B', 44C' can be adjusted, for example, by changing the widths, the thicknesses, or the constituent materials of the convex portions 44A', 44B', 44C'.

Figure 7:
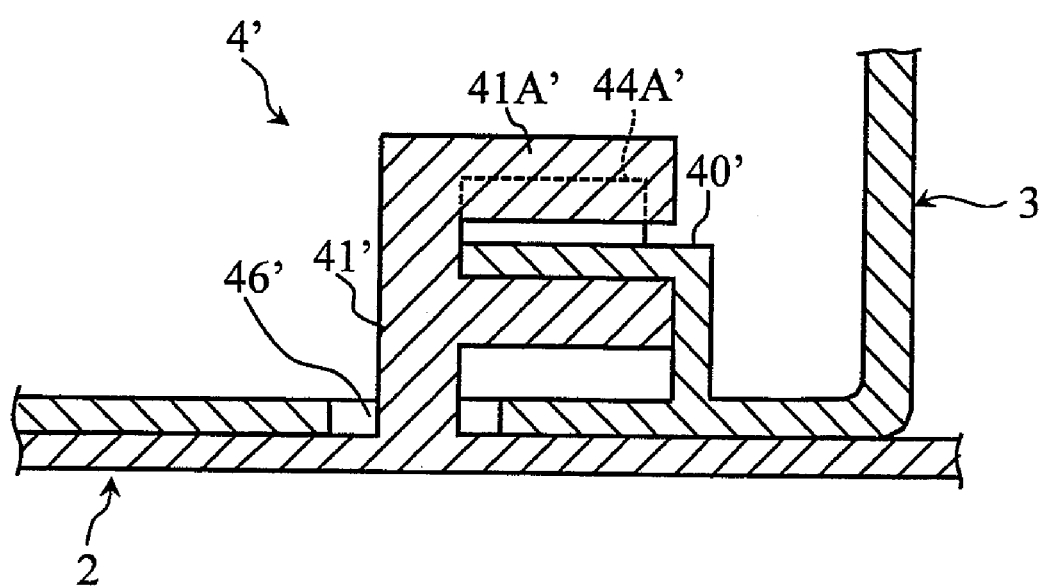
FIG. 7 is a cross sectional view along line A-A in FIG. 6A.

As shown in FIG. 7, the engagement parts 41' come into opening portions 46', respectively, which are located at a bottom portion of the blood sugar measuring device 3, so that they are placed into engagement with the rails 40', respectively. Each of the engagement parts 41' has an upper flange segment 41A'.

Figure 8:
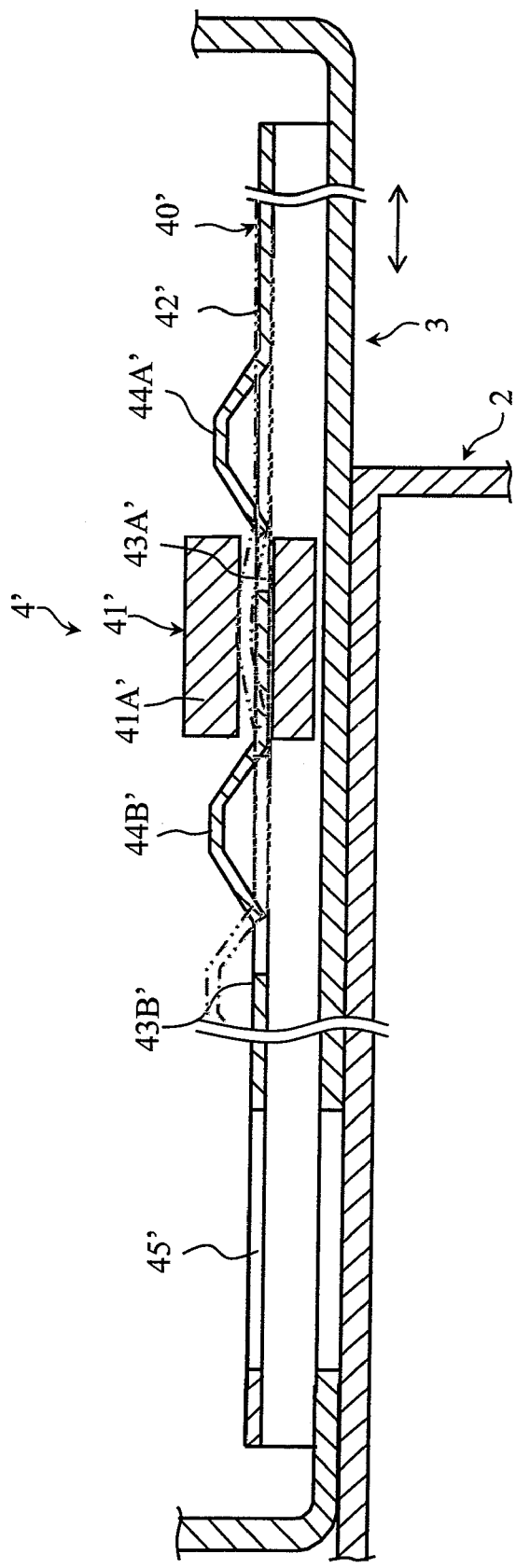
FIG. 8 is a cross sectional view along line B-B in FIG. 6A.

As shown in FIG. 8, when the blood sugar measuring device 3 is driven to move relative to the insulin dispensing device 2, the upper flange segments 41A' move along the concave portions 43A', 43B' and the convex portions 44A', 44B', 44C' in the corresponding rails 40'.

In the blood sugar level control system 1A which adopts the attachment mechanism 4', in the state shown in FIG. 6A, the engagement parts 41' are located in the smooth portions 42 of the rails 40', respectively, and the communication part 22 (the transmitting part 22A and the receiving part 22B) of the insulin dispensing device 2 is not exposed.

In case where the blood sugar measuring device 3 is driven to move relative to the insulin dispensing device 2 from the state shown in FIG. 6A, the engagement parts 41' are caused to locate in the concave portions 43A' while passing the convex portions 44A', as shown in FIG. 6B. In this case, the user can recognize by a clicking feeling that the engagement parts 41' are located in specified positions (concave portions 43A'). In addition, in the state shown in FIG. 6B, the communication part 22 of the insulin dispensing device 2 has only the transmitting part 22A exposed. As a result, in the blood sugar level control system 1A, information such as the blood sugar level, the history of insulin administration, etc., can be transmitted from the insulin dispensing device 2 to the information processing device 6.

In case where the blood sugar measuring device 3 is driven to move relative to the insulin dispensing device 2 from the state shown in FIG. 6B, the engagement parts 41' are caused to locate in the concave portions 43B' while passing the convex portions 44B', as shown in FIG. 6C. At this time, the engagement parts 41' are located in the concave portions 43B' after having gotten over the convex portions 44B', so the user can recognize by a clicking feeling that the engagement parts 41' are located in specified positions (concave portions 43B'). In the state shown in FIG. 6C, the communication part 22 (the receiving part 22B and the transmitting part 22A) of the insulin dispensing device 2 is exposed. As a result, in the blood sugar level control system 1, a signal to request the transmission of data can be transmitted from the transmitting part 22A of the insulin dispensing device 2 to the receiving part 60B of the information processing device 6, whereby data such as a change in the amount of insulin to be administered, etc., can be transmitted from the transmitting part 60A of the information processing device 6 to the receiving part 22B of the insulin dispensing device 2.

Figure 9:
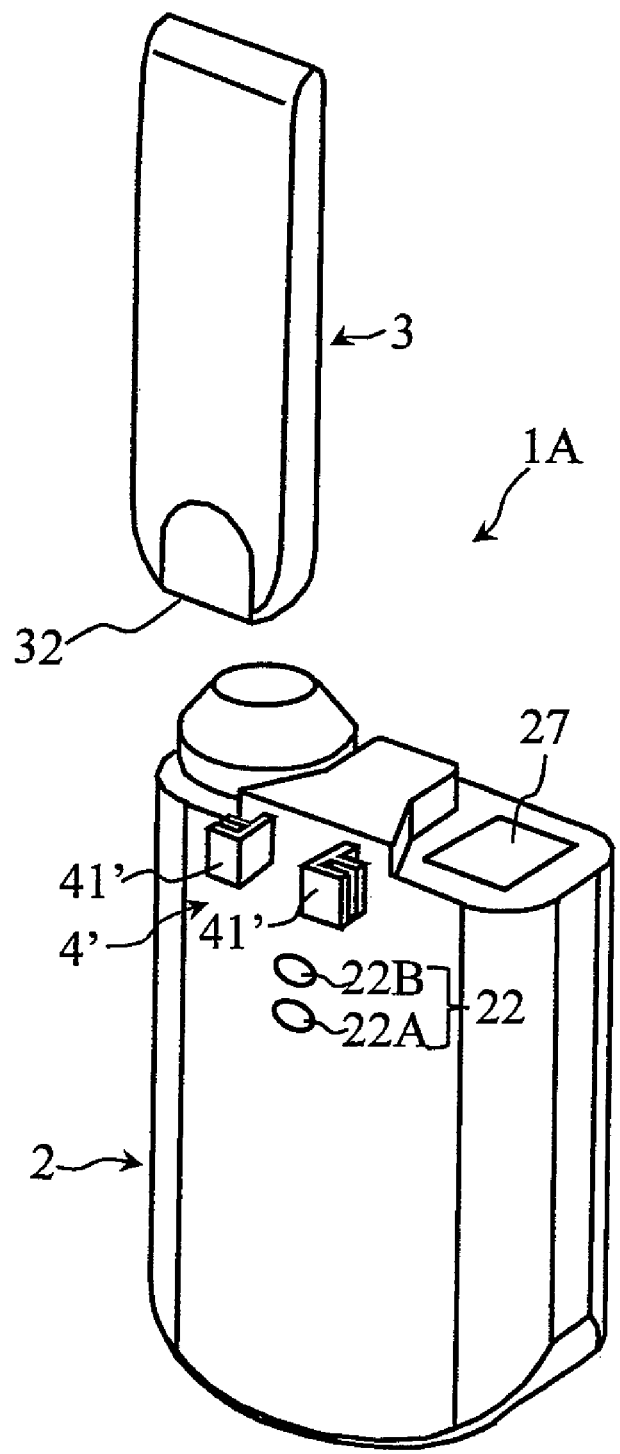
FIG. 9 is a perspective view showing a state in which the blood sugar measuring device has been separated from the insulin dispensing device in the blood sugar level control system shown in FIG. 5.

As shown in FIG. 6A through FIG. 6C, the attachment mechanism 4' is further equipped with notches 45' formed in the rails 40', respectively. These notches 45' serve to release the engagement of the rails 40' and the engagement parts 41' when the blood sugar measuring device 3 is moved relative to the insulin dispensing device 2 to a position past the convex portions 44C'. Therefore, in the attachment mechanism 4', the blood sugar measuring device 3 can be caused to separate from the insulin dispensing device 2, as shown in FIG. 9, by removing the engagement parts 41' from the rails 40' through the notches 45'. As a result of this, the burden of maintenance is reduced because the blood sugar measuring device 3 can be separated from the insulin dispensing device 2 at the time of maintenance of the blood sugar measuring device 3. In addition, if the user separates the blood sugar measuring device 3 from the insulin dispensing device 2 at the time of taking a bath, the invasion of water from the specimen insertion opening 32 of the blood sugar measuring device 3 can be prevented. Moreover, in a state in which the blood sugar measuring device 3 is separated from the insulin dispensing device 2, the communication part 22 (the receiving part 22B and the transmitting part 22A) of the insulin dispensing device 2 is exposed, similar to the state shown in FIG. 5C, so it is possible to carry out data communication between the insulin dispensing device 2 and the information processing device 6.

An attachment mechanism 4" shown in FIG. 10 through FIG. 12 serves to couple the insulin dispensing device 2 and the blood sugar measuring device 3 with each other in a relatively rotatable manner without separating the blood sugar measuring device 3 with respect to the insulin dispensing device 2.

As shown in FIG. 11 and FIG. 12, the attachment mechanism 4" is equipped with a coupling 40" which is joined to the blood sugar measuring device 3 and a bearing part 41" which is joined to the insulin dispensing device 2.

The coupling 40" has a hemispherical portion 42" and a shaft portion 43". The hemispherical portion 42" is a part that is in engagement with a bearing portion 41". The shaft portion 43" is a part that is connected with the blood sugar measuring device 3. The shaft portion 43" is provided with a plurality of protrusions 44" arranged in a circumferential direction thereof. The protrusions 44' are to bring the shaft portion 43" in fitting engagement with the blood sugar measuring device 3. These protrusions 44" have elasticity. Thus, by hardening the elasticity of the protrusions 44", it is possible to make the shaft portion 43' (the protrusions 44") less prone to disengage from the bearing portion 41" except when required.

The bearing portion 41" supports the coupling 40" in a swingable manner. This bearing portion 41' is further formed to be rotatable with respect to the housing 21 of the insulin dispensing device 2. Thus, the coupling 40" and the blood sugar measuring device 3 are made to be rotatable and swingable with respect to the insulin dispensing device 2. As a result of this, the user can turn the specimen insertion opening 32 of the blood sugar measuring device 3 in an arbitrary direction to a certain extent, so the blood drawing operation of the device at the time of measurement becomes easy.

Further, in the blood sugar control system 1A which adopts the attachment mechanism 4", by causing the blood sugar measuring device 3 to rotate relative to the insulin dispensing device 2, it is possible to make selection between a state in which the communication part 30 of the blood sugar measuring device 3 faces the receiving part 22B of the insulin dispensing device 2, as shown in FIG. 10A, and a state in which the communication part 22 of the insulin dispensing device 2 can perform communications without being interfered or blocked by the blood sugar measuring device 3, as shown in FIG. 10B. That is, in the blood sugar level measuring system 1 which adopts the attachment mechanism 4", too, it is possible to make selection between a state in which measurement data, etc., is transmitted from the blood sugar measuring device 3 to the insulin dispensing device 2, and a state in which data communication is carried out between the insulin dispensing device 2 and the information processing device 6.

As shown in FIG. 12, the blood sugar level control system 1A may be configured in such a manner that the blood sugar measuring device 3 can be removed from the coupling 40" of the insulin dispensing device 2. This system 1A can be achieved, for example, by adjusting the rigidity and/or elasticity of the plurality of protrusions 44 in the shaft portion 43". By making it possible to attach and detach the blood sugar measuring device 3 to and from the insulin dispensing device 2, the maintenance of the blood sugar measuring device 3 can be made easy, and the invasion of water from the specimen insertion opening 32 can be prevented at the time of bathing.

Next, a second embodiment of the present invention will be described while referring to FIG. 13 through FIG. 15. However, in these figures, the same symbols are attached to like elements to those in the blood sugar level control system 1A which has previously explained with reference to FIG. 1 through FIG. 12, and a duplication explanation thereof in the following will be omitted.

Figure 13A:
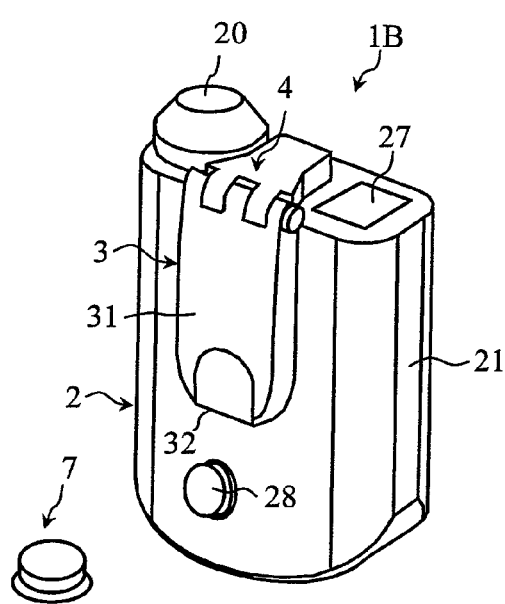
FIG. 13A and FIG. 13B are perspective views showing a blood sugar level control system according to a second embodiment of the present invention.
Figure 13B:
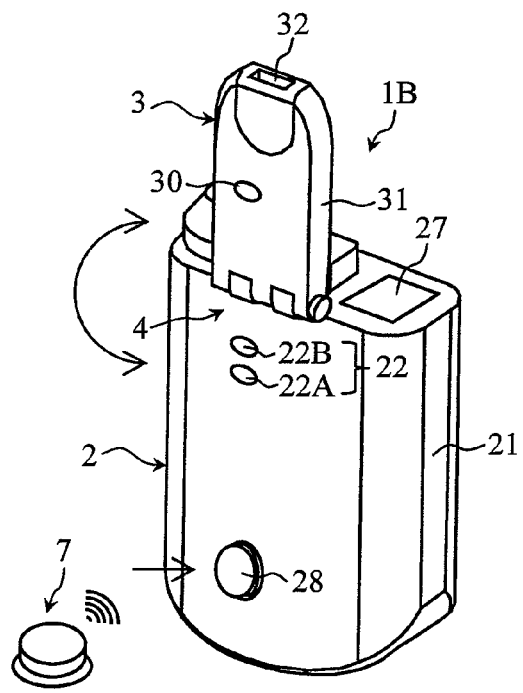
Figure 14:
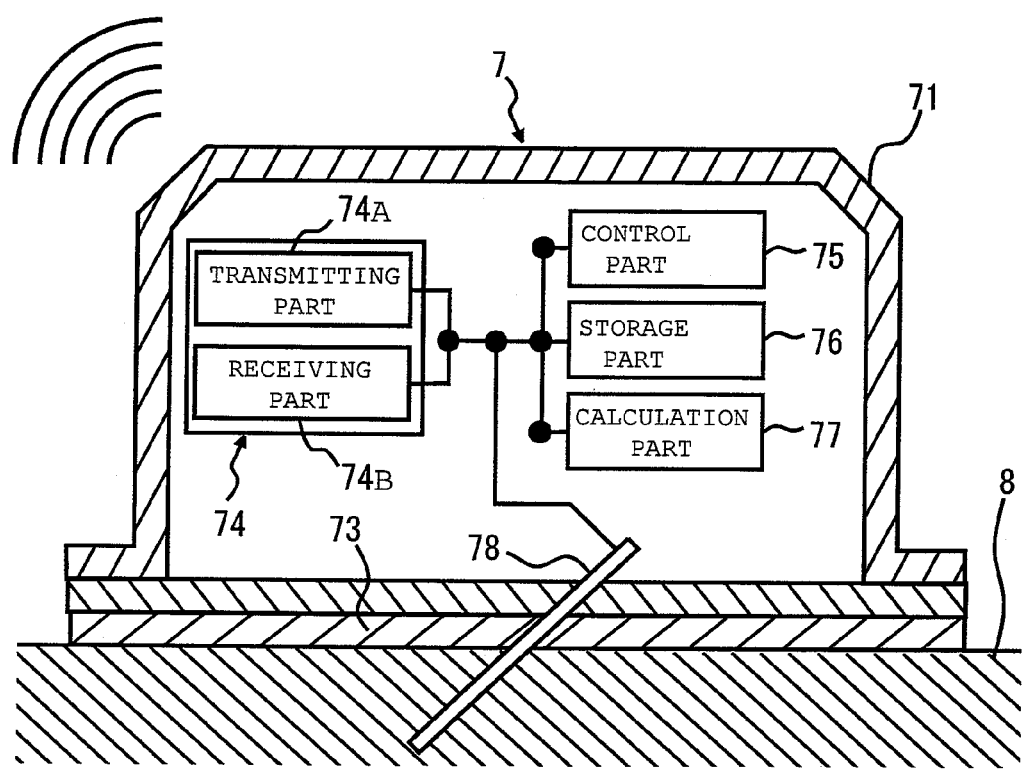
FIG. 14 is a cross sectional view explaining a body-implanted type continuous blood sugar measuring device which constitutes the blood sugar level control system shown in FIG. 13.

As shown in FIG. 13A and FIG. 13B, a blood sugar level control system 1B includes an insulin dispensing device 2, a blood sugar measuring device 3, and a body-implanted type continuous blood sugar measuring device 7. The insulin dispensing device 2 is so configured as to be able to perform wireless data communication with the continuous blood sugar measuring device 7.

In the blood sugar level control system 1B shown in FIG. 13A and FIG. 13B, the insulin dispensing device 2 and the blood sugar measuring device 3 are coupled together by means of the attachment mechanism 4 which has been previously explained with reference to FIG. 4. In a state shown in FIG. 13A, the blood sugar measuring device 3 and the insulin dispensing device 2 are folded with respect to each other, so that measurement data, etc., can be transmitted from the blood sugar measuring device 3 to the insulin dispensing device 2. In a state shown in FIG. 13B, the blood sugar measuring device 3 and the insulin dispensing device 2 are opened or unfolded with respect to each other, so that data communication can be made between the insulin dispensing device 2 and the continuous blood sugar measuring device 7.

Of course, the coupling of the insulin dispensing device 2 and the blood sugar measuring device 3 may be carried out by means of the attachment mechanism 4', which has been explained with reference to FIG. 7 and FIG. 8, or by means of the attachment mechanism 4", which has been explained with reference to FIG. 11, in place of the attachment mechanism 4.

The continuous blood sugar measuring device 7 corresponds to a second blood sugar measuring device, and is used while being fixed to the skin of an abdominal part, a shoulder, an arm or the like of a diabetic patient. As shown in FIG. 14, the continuous blood sugar measuring device 7 is provided with a housing 71, a substrate 72, an adhesive layer 73, and a sensor 78.

The housing 71 is formed into a cap shape having a lower aperture. It is preferable that this housing 71 have a waterproof property or a water resistant property. Such a housing 71 is formed of an extremely low permeable material such as for example metal, polypropylene (PP) resin, or the like.

The substrate 72 is to close the lower aperture of the housing 71. This substrate 72 is equipped with wiring formed into a pattern, and a variety of kinds of electronic parts mounted thereon. The substrate 72 functions as a calculation part 75, a storage part 76, and a control part 77, all of which will be described later.

The adhesive layer 73 is to fix the continuous blood sugar measuring device 7 to a skin, and is fixedly secured to the substrate 72. This adhesive layer 73 is formed of a material having adhesion such as for example a double-faced adhesive tape, etc.

The sensor 78 is to collect data relevant to the blood sugar level. This sensor 78 extends through the substrate 72 and the adhesive layer 73, and one end portion of the sensor 78 is implanted in the inside of the skin. On the other hand, the other end portion of the sensor 78 is protruded into the interior of the housing 71, and the sensor 78 is electrically connected at its other end portion to the substrate 72. As the sensor 78, there is used one that detects, for example, the amount of charge transfer resulting from enzymatic reactions. Though not shown, the sensor 78 is equipped with electrodes formed on the substrate, which include a working electrode and an opposite electrode. The electrodes may further include a reference electrode. An enzyme such as glucose dehydrogenase, which is an oxidation-reduction enzyme, is fixed on the electrodes. The enzyme reacts with glucose in body fluid such as interstitial fluid inside the skin. When a constant voltage is applied between the working electrode and the opposite electrode of the sensor 78, a response current corresponding to the amount of reaction of glucose will flow therebetween.

The continuous blood sugar measuring device 7 further has a communication part 74, a calculation part 75, a storage part 76, and a control part 77.

The communication part 74 is provided with a transmitting part 74A and a receiving part 74B, and has a function of receiving a command from the insulin dispensing device 2, and transmitting data to the insulin dispensing device 2. This communication part 74 is able to perform data transmission and reception through the use of infrared light. Of course, for the purpose of transmission and reception of data through the communication part 74, light of other frequencies (wavelengths), a radio wave such as a 2.45 GHz band adopted in Bluetooth, may be used.

Here, the data transmitted from the continuous blood sugar measuring device 7 to the insulin dispensing device 2 through the transmitting part 74A may be raw data such as a response current value obtained through the sensor 8, data obtained by converting the raw data into other physical quantities such as a voltage value, data with respect to the calculated result of the blood sugar level, and data obtained by correcting the raw data and blood sugar level calculation data. Data may be transmitted to the blood sugar measuring device 3 instead of the insulin dispensing device 2. In this case, the data from the continuous blood sugar measuring device 7 is further transmitted from the blood sugar measuring device 3 to the insulin dispensing device 2.

The calculation part 75 calculates the blood sugar level based on the data obtained from the sensor 78. The calculation of the blood sugar level is performed by applying calibration curve data and correction data to the raw data (or conversion data which is obtained through the conversion of the raw data). However, the calculation of the blood sugar level from the measured data may also be carried out in the insulin dispensing device 2 (the blood sugar measuring device 3) to which the measured data is to be transmitted.

The storage part 76 is to store data required for the measurement of the blood sugar level, e.g., measurement data such as a current value, etc., data with respect to a calibration curve, and correction data. In addition, this storage part 76 can also store the blood sugar level calculated in the continuous blood sugar measuring device 7.

The control part 77 controls the operations of the respective parts (e.g., data collection by the implanted type sensor 78, data transmission from the transmitting part 74A, data reception in the receiving part 74B, or the calculation operation of the blood sugar level in the calculation part 75).

Figure 15:
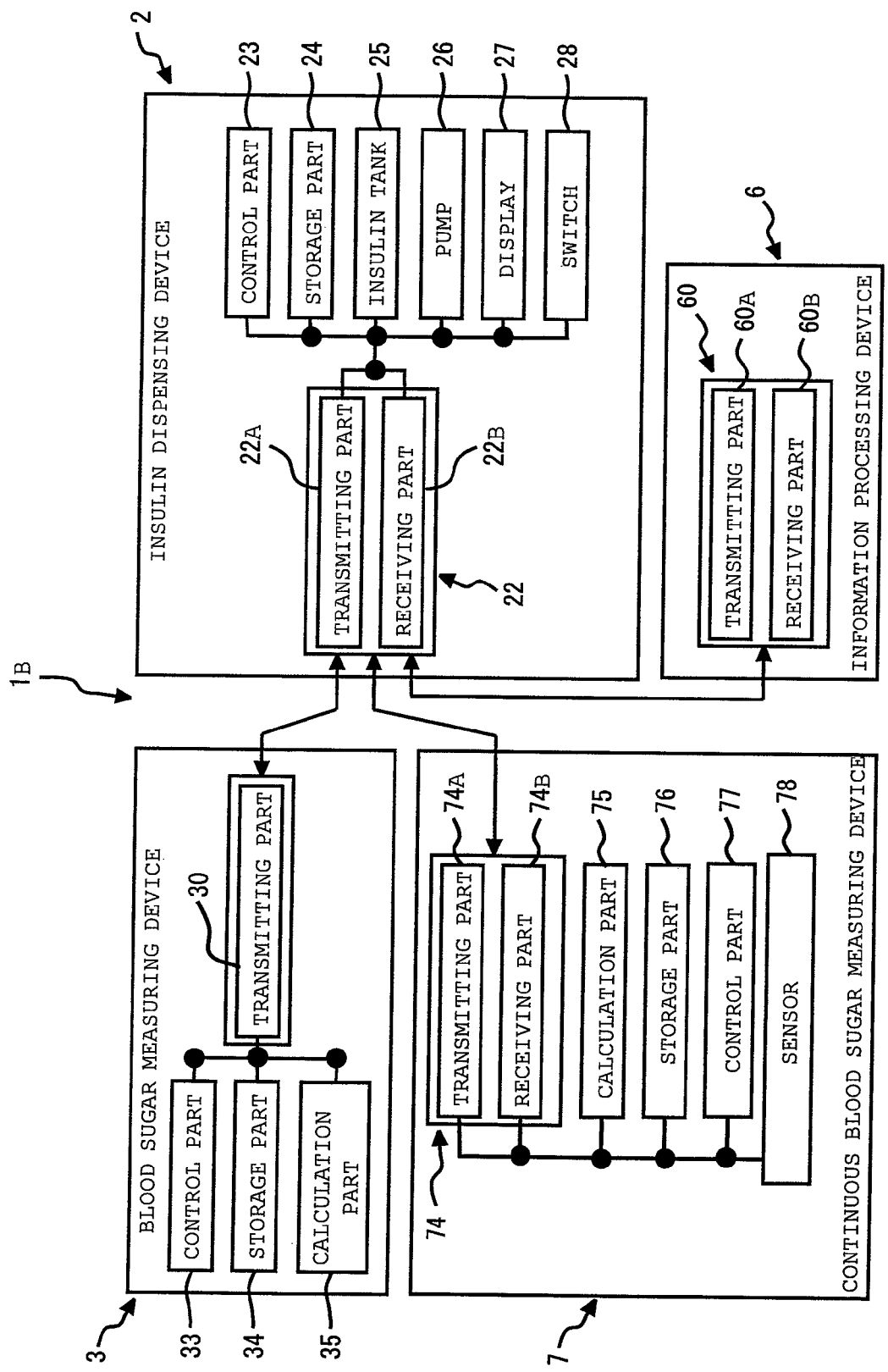
FIG. 15 is a block diagram showing the blood sugar level control system shown in FIG. 13, together with an information processing unit.

As shown in FIG. 15, the insulin dispensing device 2 can receive measurement data, etc., from the blood sugar measuring device 3, and can transmit and receive measurement data, etc., to and from the continuous blood sugar measuring device 7 and the external information processing device 6.

As shown in FIG. 13A, FIG. 13B and FIG. 15, the insulin dispensing device 2 has a switch 28. This switch 28 is to select an object which performs data communication with the insulin dispensing device 2, and is arranged on the housing 21 of the insulin dispensing device 2. More specifically, the switch 28 can select a state from a state in which the insulin dispensing device 2 can perform data communication with the blood sugar measuring device 3, a state in which the insulin dispensing device 2 can perform data communication with the continuous blood sugar measuring device 7, and a state in which the insulin dispensing device 2 can perform data communication with the external information processing device 6. The switch 28 may further be one which can also select a state in which the insulin dispensing device 2 can not perform data communication with any of the blood sugar measuring device 3, the continuous blood sugar measuring device 7 and the external information processing device 6. In addition, although communication between the insulin dispensing device 2 and communication objects may be carried out by adopting the same frequency band to the plurality of devices, different frequency bands may be used according to the communication objects.

In the blood sugar level control system 1B, the blood sugar level is continuously measured by the continuous blood sugar measuring device 7. More specifically, in the continuous blood sugar measuring device 7, a fixed voltage is continuously applied between the working electrode and the opposite electrode of the sensor 78. As a result, a response current corresponding to a glucose concentration is outputted from the sensor 78. This output is converted into a corresponding blood sugar level by the calculation part 75.

The calculated blood sugar level data is transmitted to the insulin dispensing device 2 through the transmitting part 74A of the continuous blood sugar measuring device 7 and the receiving part 22B of the insulin dispensing device 2. Blood sugar level data is stored in the storage part 24 of the insulin dispensing device 2. In the insulin dispensing device 2, the control part 23 determines whether the insulin administration to the inside of a patient's body is necessary, and if necessary, calculates an amount of insulin based on the measurement data, and administers the calculated amount of insulin to the patient by controlling the pump 26. As a result, according to the insulin dispensing device 2, it is possible to inject insulin into the inside of the body based on the change over time of the blood sugar level under nearer physiological conditions, and for this reason, the blood sugar level can be maintained within a desired range in an effective manner.

In the blood sugar level control system 1B, the blood sugar level is further measured by the blood sugar measuring device 3, as necessary. The blood sugar level measured by the blood sugar measuring device 3 is stored in the storage part 34, and is compared with the blood sugar level, which is measured by the continuous blood sugar measuring device 7, by the calculation part 35. In cases where a deviation between the blood sugar levels measured by the blood sugar measuring device 3 and the continuous blood sugar measuring device 7 is large, the calibration of the continuous blood sugar measuring device 7 is carried out.

More specifically, the measurement data (or data representing the blood sugar level) with respect to the blood sugar level measured in the continuous blood sugar measuring device 7 is transmitted from the continuous blood sugar measuring device 7 to the blood sugar measuring device 3 directly or through the insulin dispensing device 2. This measurement data may be transmitted from the continuous blood sugar measuring device 7 to the blood sugar measuring device 3 in a continuous manner, or at the same timing as that at which the blood sugar level is measured in the blood sugar measuring device 3.

In the blood sugar measuring device 3, the calculation part 35 makes a comparison between the blood sugar levels measured in the blood sugar measuring device 3 and the continuous blood sugar measuring device 7. In cases where the difference of those values is beyond constant value as a result of a comparison, the calculation part 35 creates the correction data according to the difference of both blood sugar levels. This correction data is transmitted to the continuous blood sugar measuring device 7, and it is referred to at the time when the blood sugar level is calculated in the continuous blood sugar measuring device 7.

Of course, the creation of the correction data according to the blood sugar levels measured in the blood sugar measuring device 3 and the continuous blood sugar measuring device 7 may be carried out in the insulin dispensing device 2 or in the continuous blood sugar measuring device 7. In addition, in the insulin dispensing device 2 or the blood sugar measuring device 3, you may perform the correction of the blood sugar level.

If the correction data is created in this manner, and if the blood sugar level obtained in the continuous blood sugar measuring device 7 is corrected by the use of the correction data thus created, it is possible to make an exact blood sugar level measurement even if the enzyme fixed on the sensor 78 will deteriorate due to the passage of time.

Next, a third embodiment of the present invention will be described while referring to FIG. 16 and FIG. 17. However, in these figures, the same symbols are attached to the same or similar elements to those in the blood sugar level control system which has previously explained with reference to FIG. 1 through FIG. 12, and a duplication explanation thereof in the following will be omitted.

Figure 16A:
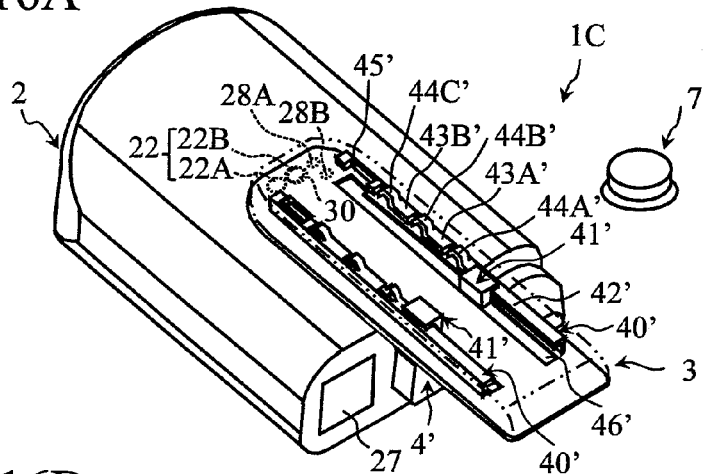
FIG. 16A through FIG. 16C are perspective views showing a blood sugar level control system according to a third embodiment of the present invention.
Figure 16B:
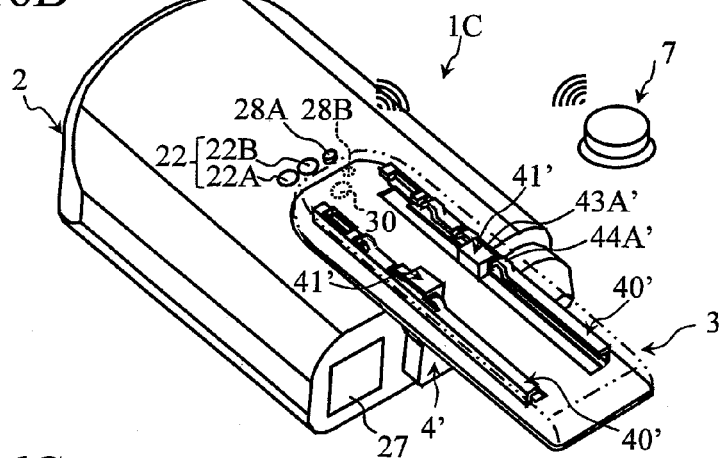
Figure 16C:
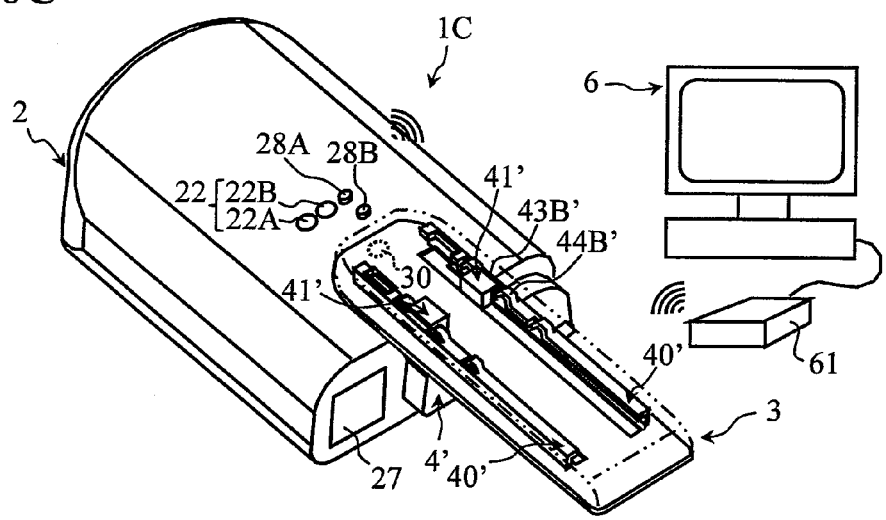
Figure 17:
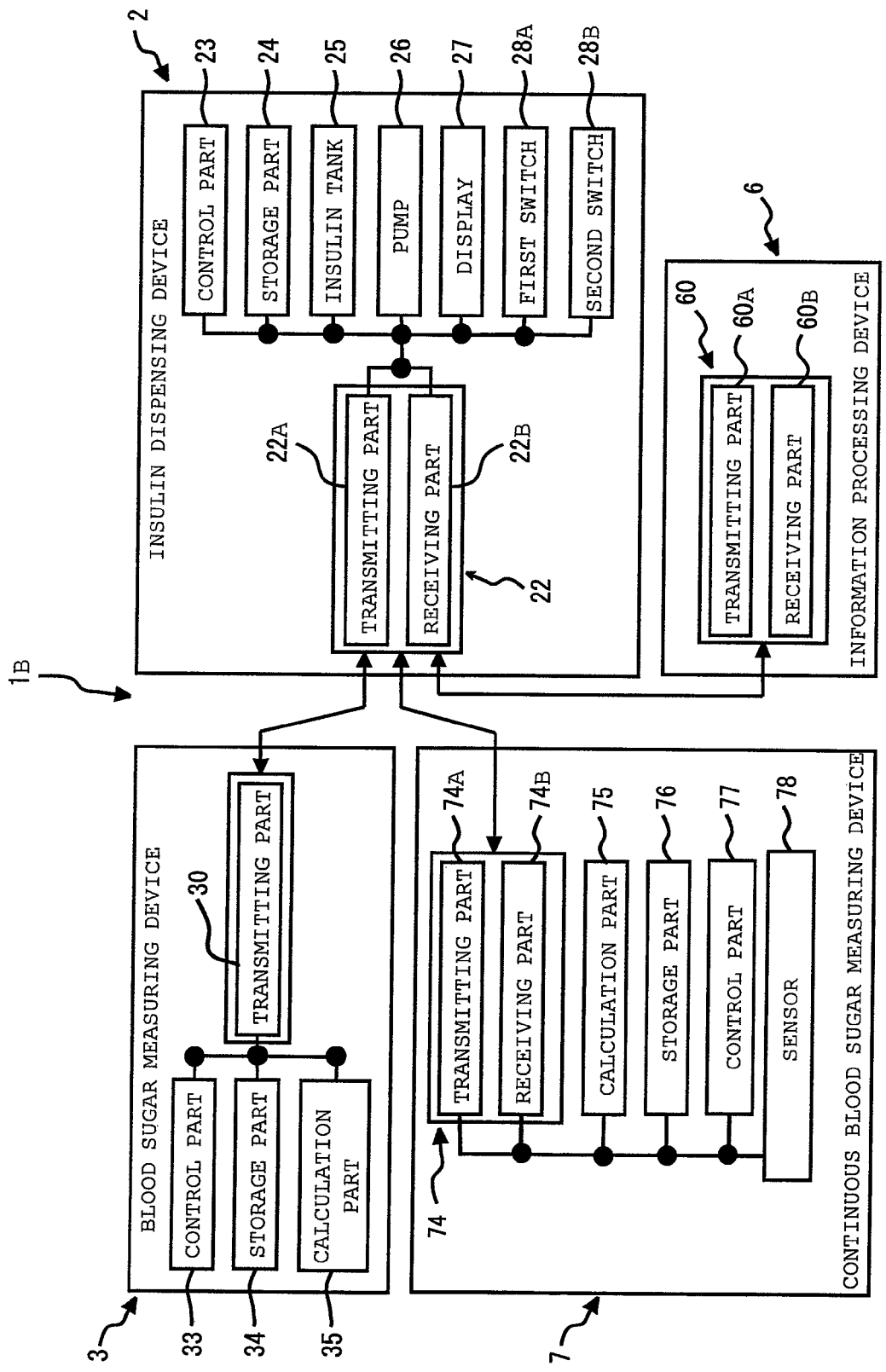
FIG. 17 is a block diagram showing the blood sugar level control system shown in FIG. 16, together with an information processing unit.

A blood sugar level control system 1C shown in FIG. 16A through FIG. 16C includes an insulin dispensing device 2, a blood sugar measuring device 3, and a continuous blood sugar measuring device 7, as in the blood sugar level control system 1B (see FIG. 13 through FIG. 15) previously explained. However, in the blood sugar level control system 1C, the insulin dispensing device 2 and the blood sugar measuring device 3 are coupled with each other by means of the attachment mechanism 4' (see FIG. 6) previously explained, in such a manner that they are mutually slidable with respect to each other. As stated above, the attachment mechanism 4' includes engagement parts 41' fixed to the insulin dispensing device 2, and rails 40' fixed to the blood sugar measuring device 3.

The blood sugar level control system 1C is further different in the insulin dispensing device 2 with respect to the blood sugar level control system 1B (see FIG. 13 through FIG. 15) previously explained.

First, the blood sugar level control systems 1C is different from the blood sugar level control system 1B (see FIG. 13 through FIG. 15) in that the insulin dispensing device 2 has a transmitting part 22A and a receiving part 22B arranged side by side in a direction perpendicular to the direction of movement of the blood sugar measuring device 3.

Further, the blood sugar level control system 1C is different from the blood sugar level control system 1B (see FIG. 13 through FIG. 15) in that a first switch 28A and a second switch 28B are provided on the insulin dispensing device 2. These switches 28A, 28B are caused to turn on and off according to the movement of the blood sugar measuring device 3. That is, when the blood sugar measuring device 3 lies above the first and second switches 28A, 28B, the first and second switches 28A, 28B are in depressed states, so that they are placed into on states. On the other hand, when the blood sugar measuring device 3 does not lie above the first and second switches 28A, 28B, the first and second switches 28A, 28B are in undepressed states, so that the first and second switches 28A, 28B are placed into off states.

The first and second switches 28A, 28B are arranged side by side in the direction of movement of the blood sugar measuring device 3 with respect to the insulin dispensing device 2. The center to center distance between the first and second switches 28A, 28B corresponds to the center to center distance of concave portions 43A', 43B' in the rails 40'. Thus, the first and second switches 28A, 28B can take three modes shown in FIG. 16A through FIG. 16C, according to the position of the blood sugar measuring device 3 (i.e., the positions of the engagement parts 41' with respect to the rails 40'), the three modes being as follows: both of the first and second switches 28A, 28B are in on states; the first switch 28A is in an off state, and the second switch 28B is in an on state; and both of the first and second switches 28A, 28B are in off states.

In the state shown in FIG. 16A, the engagement parts 41' are located in the smooth portions 42 of the rails 40' in the attachment mechanism 4'. In this state, both of the first and second switches 28A, 28B are pushed into the on states by means of the blood sugar measuring device 3. On the other hand, the communication part 22 (the transmitting part 22A and the receiving part 22B) of the insulin dispensing device 2 is not exposed, and the receiving part 22B of the insulin dispensing device 2 faces (opposes) the transmitting part 30 of the blood sugar measuring device 3.

In the state shown in FIG. 16B, the engagement parts 41' are located in first concave portions 43A' in the attachment mechanism 4'. In this state, the blood sugar measuring device 3 exists only on the second switch 28B among the first switch 28A and the second switch 28B. Therefore, the first switch 28A is placed into the off state, and the second switch 28B is placed into the on state. Further, the communication part 22 (the transmitting part 22A and the receiving part 22B) of the insulin dispensing device 2 is exposed.

In the state shown in FIG. 16C, the engagement parts 41' are located in second concave portions 43B' in the attachment mechanism 4'. In this state, the first switch 28A and the second switch 28B are both in the off states, and the communication part 22 (the transmitting part 22A and the receiving part 22B) of the insulin dispensing device 2 is exposed.

As described above, there are three kinds of combinations of the on state and the off state of the first switch 28A and the second switch 28B in the insulin dispensing device 2 according to the position of the blood sugar measuring device 3. Therefore, it is possible to perform data communication by selecting a specific one from the three kinds of communication objects, as a communication object for the insulin dispensing device 2, according to combinations of the on and off states of the first and second switches 28A, 28B.

For example, when both of the first and second switches 28A, 28B are in the on states (see FIG. 16A), the communication part 22 (the transmitting part 22A and the receiving part 22B) of the insulin dispensing device 2 is not exposed, and the receiving part 22B of the insulin dispensing device 2 faces the transmitting part 30 of the blood sugar measuring device 3. Accordingly, it can be constructed that when both of the first and second switches 28A, 28B are in the on states, the insulin dispensing device 2 selects the blood sugar measuring device 3 as a communication object, and performs data communication with the blood sugar measuring device 3.

On the other hand, in the states of FIG. 16B and FIG. 16C, the communication part 22 (the transmitting part 22A and the receiving part 22B) of the insulin dispensing device 2 is exposed, so the insulin dispensing device 2 can perform data communication with the information processing device 6 or the continuous blood sugar measuring device 7. Accordingly, when the first switch 28A is in the off state and the second switch 28B is in the on state, for example, the continuous blood sugar measuring device 7 (or the external information processing device 6) can be selected as a communication object with the insulin dispensing device 2, whereas when both of the first and second switches 28A, 28B are in the off states, the external information processing device 6 (or continuous blood sugar measuring device 7) can be selected as a communication object of the insulin dispensing device 2.

The blood sugar level control system 1C is usually placed in the state shown in FIG. 16B, for example. That is, the communication part 22 of the insulin dispensing device 2 is exposed, and at the same time, the first switch 28A is placed into the off state, and the second switch 28B is placed into the on state. At this time, in the insulin dispensing device 2, the control part 23 grasps that the first switch 28A is in the off state and the second switch 28B is in the on state. As a result, the insulin dispensing device 2 is brought by the control part 23 into a state in which it receives the data transmitted from the continuous blood sugar measuring device 7, and carries out processing according to the data thus received.

On the other hand, in cases where the insulin dispensing device 2 is caused to perform data communication with the blood sugar measuring device 3, the blood sugar measuring device 3 is moved with respect to the insulin dispensing device 2 so that they are brought into the state shown in FIG. 16A from the state shown in FIG. 16B. Such a movement of the blood sugar measuring device 3 is carried out by the manual operation of the user. Of course, it may be constructed such that by operating a button (not shown), the blood sugar measuring device 3 is driven to move to a prescribed position.

In the state shown in FIG. 16A, the first and second switches 28A, 28B are both in the on states, and at the same time, the insulin dispensing device 2 and the blood sugar measuring device 3 are in a state in which they can perform data communication with each other. Therefore, it is grasped by the control part 23 that the first and second switches 28A, 28B are both in the off states, and the insulin dispensing device 2 is placed into a state in which it performs transmission and reception of data with the blood sugar measuring device 3, so that it carries out processing according to the data communication. The insulin dispensing device 2 receives the blood sugar level which has been measured in the blood sugar measuring device 3, for example. The data transmitted to the insulin dispensing device 2 is transmitted from the insulin dispensing device 2 to the continuous blood sugar measuring device 7 as untouched data or calibration data which has been created based on that data, by placing the insulin dispensing device 2 and the blood sugar measuring device 3 into the state shown in FIG. 16B.

In addition, in cases where the insulin dispensing device 2 performs data communication with the external information processing device 6, the insulin dispensing device 2 and the blood sugar measuring device 3 are placed into the state shown in FIG. 16C. In the state shown in FIG. 16C, the first and second switches 28A, 28B are both in the off states, and at the same time, the communication part 22 (the transmitting part 22A and the receiving part 22B) is exposed. Therefore, it is grasped by the control part 23 that the first and second switches 28A, 28B are both in the off states, and the insulin dispensing device 2 is placed into a state in which it performs transmission and reception of data with the external information processing device 6, so that it carries out processing according to the data communication. As a result of this, the administration history of insulin in the insulin dispensing device 2 and the measurement result (blood sugar level) in the continuous blood sugar measuring device 3 can be transmitted to the external information processing device 6.

Thus, the blood sugar level control system 1C has a configuration capable of selecting a communication object for the insulin dispensing device 2 by only selecting the position of the blood sugar measuring device 3 with respect to the insulin dispensing device 2 (a combination of the on and off states of the first and second switches 28A, 28B) manually.

The invention claimed is:

1. A blood sugar level control system comprising:
    a blood sugar measuring device to measure a blood sugar level, the blood sugar measuring device having a first wireless data transmitting part provided on a surface thereof, the first wireless data transmitting part being for transmitting data relating to the blood sugar level;
    an insulin dispensing device to administer insulin into a body, the insulin dispensing device having a wireless data communication unit provided on a surface thereof, the wireless data communication unit including a second wireless data transmitting part for transmitting data to an external information processing device, and a wireless data receiving part for receiving data from the first wireless data transmitting part and the external information processing device; and
    an attachment mechanism to couple the insulin dispensing device and the blood sugar measuring device so that the blood sugar measuring device is movable, without separating from the insulin dispensing device, among at least a first position in which the wireless data receiving part of the insulin dispensing device is covered with the blood sugar measuring device in a way that the first wireless data transmitting part of the blood sugar measuring device faces the wireless data receiving part of the insulin dispensing device, and a second position in which the second wireless data transmitting part and the wireless data receiving part of the insulin dispensing device are not covered with the blood sugar measuring device.

2. The blood sugar level control system as set forth in claim 1,
    wherein the attachment mechanism couples the insulin dispensing device and the blood sugar measuring device so that the blood sugar measuring device is movable among at least the first position, the second position, and a third position, which is different from the second position, in which the second wireless data transmitting part of the insulin dispensing device is not covered with the blood sugar measuring device, and
    the insulin dispensing device is further provided with a selection unit that selects the blood sugar measuring device, the external information processing device, and a second blood sugar measuring device as a communication object of the wireless communication unit when the blood sugar measuring device is at the first position, the second position, and the third position, respectively.

3. The blood sugar level control system as set forth in claim 1, wherein said blood sugar measuring device and said insulin dispensing device are each provided with a housing having a waterproof property or a water resistant property.

4. The blood sugar level control system as set forth in claim 3,
wherein said blood sugar measuring device is provided with an insertion opening through which a specimen is inserted, and a closing unit that closes said insertion opening.

5. The blood sugar level control system as set forth in claim 1, further comprising:
a second blood sugar measuring device that is used while being implanted in the inside of said body;
wherein at least one of said blood sugar measuring device and said insulin dispensing device is constructed so as to be able to perform data communication with said second blood sugar measuring device.

6. The blood sugar level control system as set forth in claim 5,
wherein the second wireless data transmitting part is able to perform data communication with said second blood sugar measuring device; and
said insulin dispensing device is further provided with a selection unit that selects said blood sugar measuring device or said second blood sugar measuring device as a communication object.

7. The blood sugar level control system as set forth in claim 6,
wherein said selection unit is constructed so as to be able to select said information processing unit as said communication object.

8. The blood sugar level control system as set forth in claim 6,
wherein said selection unit is a switch that is arranged in said insulin dispensing device.

9. The blood sugar level control system as set forth in claim 6,
wherein said selection unit selects said communication object according to the relative position of said blood sugar measuring device with respect to said insulin dispensing device.

10. The blood sugar level control system as set forth in claim 9,
said selection unit includes a plurality of switches, and selects said communication object according to combinations of an on state or an off state of each of said plurality of switches.

* * * * *